US009170180B2

(12) United States Patent
Shinohara et al.

(10) Patent No.: US 9,170,180 B2
(45) Date of Patent: Oct. 27, 2015

(54) PARTICLE NUMBER COUNTING APPARATUS

(71) Applicant: HORIBA, Ltd., Kyoto (JP)

(72) Inventors: Masayoshi Shinohara, Kyoto (JP); Yoshinori Otsuki, Kyoto (JP); Kenji Kondo, Kyoto (JP); Kazuo Hanada, Kyoto (JP); Steve Kerrigan, St. Anthony Village, MN (US)

(73) Assignee: Horiba, Ltd., Kyoto (JP)

( * ) Notice: Subject to any disclaimer, the term of this patent is extended or adjusted under 35 U.S.C. 154(b) by 284 days.

(21) Appl. No.: 13/723,371

(22) Filed: Dec. 21, 2012

(65) Prior Publication Data

US 2013/0180321 A1    Jul. 18, 2013

(30) Foreign Application Priority Data

Dec. 22, 2011  (JP) .................................. 2011-282102

(51) Int. Cl.
*G01N 33/00* (2006.01)
*G01N 1/40* (2006.01)
*G01N 15/06* (2006.01)

(52) U.S. Cl.
CPC ................ *G01N 1/40* (2013.01); *G01N 15/065* (2013.01)

(58) Field of Classification Search
CPC .................................. G01N 37/00; G01N 1/40
USPC .......... 73/23.42, 28.01, 28.04, 61.72, 863.21, 73/863.23; 118/715, 716, 726; 137/560; 356/37
See application file for complete search history.

(56) References Cited

U.S. PATENT DOCUMENTS

| 4,790,650 | A | * | 12/1988 | Keady .............................. 356/37 |
| 5,026,155 | A | | 6/1991 | Ockovic et al. |
| 5,118,959 | A | * | 6/1992 | Caldow et al. ................. 250/573 |
| 5,239,356 | A | | 8/1993 | Hollander et al. |
| 5,872,622 | A | | 2/1999 | Schildmeyer et al. |

(Continued)

FOREIGN PATENT DOCUMENTS

| JP | 03-099248 A | 4/1991 |
| JP | 07044775 U | 11/1995 |

(Continued)

OTHER PUBLICATIONS

Notice of reasons for refusal dated Mar. 5, 2015 issued in Japanese patent application No. 2011-282102.

*Primary Examiner* — Hezron E Williams
*Assistant Examiner* — Hoang Nguyen
(74) *Attorney, Agent, or Firm* — Craig J. Lervick; Larkin Hoffman Daly & Lindgren, Ltd.

(57) ABSTRACT

To improve an offset accuracy in a particle number counting apparatus (100) condensing a working liquid with sample particles, the apparatus including:
a porous member (22) in which a flow path (23) is passed through to form an inlet (23*a*) at a lower side and an outlet (23*b*) at an upper side thereof so that the working liquid is supplied to a predetermined section of the porous member so as to be impregnated into the entire part of the porous member; and a housing (21) having an accommodating space for accommodating the porous member (22), wherein a gap (S) is formed between an outer peripheral surface (22*a*) of the porous member (22) and an inner peripheral surface (21*b*) of the accommodating space of the housing (21) at least in an upper side than the predetermined section to be supplied with the working liquid.

16 Claims, 6 Drawing Sheets

(56) References Cited

U.S. PATENT DOCUMENTS

| | | |
|---|---|---|
| 6,639,671 B1 * | 10/2003 | Liu .................................. 356/336 |
| 6,980,284 B2 | 12/2005 | Ahn et al. |
| 7,605,910 B2 * | 10/2009 | Ahn .................................. 356/37 |
| 7,777,867 B2 * | 8/2010 | Hopke et al. ...................... 356/37 |
| 8,208,132 B2 * | 6/2012 | Huetter et al. .................... 356/37 |
| 8,869,593 B2 * | 10/2014 | Gorbunov et al. ............ 73/28.01 |
| 2003/0202169 A1 * | 10/2003 | Liu .................................. 356/37 |
| 2011/0056273 A1 | 3/2011 | Gorbunov et al. |
| 2014/0033915 A1 * | 2/2014 | Hering et al. ......................... 95/1 |
| 2015/0160105 A1 * | 6/2015 | Caldow et al. ............... 73/61.72 |

FOREIGN PATENT DOCUMENTS

| | | |
|---|---|---|
| JP | 2010-164566 A | 7/2010 |
| JP | 2011521213 A | 7/2011 |
| JP | 2011243552 A | 12/2011 |
| WO | 2009136166 A1 | 11/2009 |
| WO | WO2012/142297 A1 | 10/2012 |

* cited by examiner

PARTICLE NUMBER COUNTING APPARATUS

CLAIM OF PRIORITY

The present application claims priority to Japanese Patent Application No. 2011-282102, filed Dec. 22, 2011, the disclosure of which is hereby incorporated by reference in its entirety.

TECHNICAL FIELD

The present invention generally relates to a particle number counter and, in particular, relates to a particle number counting apparatus condensing a working liquid with sample particles to be measured as cores that are enlarged in diameter and the number thereof is thereafter counted by a laser optical system, signal processing and the like.

BACKGROUND ART

A particle counting apparatus of this kind, as disclosed in Patent Literature 1, provides a measurement targeted gas containing sample particles to flow in a flow path in which a working liquid (alcohol such as ethanol, isopropanol, and butanol) is diffused in a state of saturated vapor and the working liquid is thereafter condensed by cooling with the sample particles as cores to produce droplets of the working liquid so that the number of the sample particles is counted by counting the droplets of the working Liquid to thereby measure a concentration thereof.

In a conventional construction of a particle counting apparatus as shown in e.g. FIG. 9, however, in order to fill the flow path with the saturated vapor of the working liquid, a porous member including the flow path vertically passed therethrough is inserted into a cylindrical housing to be fitted, and lower end portions of the porous member are immersed in the working liquid so that the working liquid is impregnated into the entire part of the porous member, and therefore the flow path penetrating the porous member is brought into the condition of being saturated with the vapor of the working liquid.

SUMMARY OF INVENTION

In the construction mentioned above, however, when a pressure at an inlet of the apparatus changes, there may be a case where particles are counted even when sample particles are not introduced and measurement errors occur due to the unknown cause of inside of the apparatus.

As a result of intensive studies, the present inventor has tracked down the fact that, there occurs a phenomenon such as a capillary phenomenon between an outer peripheral surface of the porous member and an inner peripheral surface of the housing, and the working liquid reaches the top surface of the porous member in a route as shown by an arrow in FIG. 9, leaking into the flow path in a liquid state so that the droplets are produced to be counted. Usually, since the porous member is porous and impregnated with the working liquid, it is very likely that an action such as a capillary phenomenon occurs between the outer peripheral surface thereof and the inner peripheral surface of the housing.

The present invention has been made based on the findings as mentioned above, and an essential object thereof is to attain a high measurement accuracy in a particle number counting apparatus of this kind, in particular, with reduction of an offset error as much as possible even when the pressure at the inlet of the apparatus changes.

Solution to Problem

That is, a particle number counting apparatus according to the present invention includes: a saturator part including a flow path in which a working liquid is diffused in a vaporized state so as to render sample particles contained in a measurement targeted gas to flow in the flow path; a condenser part for introducing the sample particles and vaporized working liquid from the flow path and condensing the working liquid with the sample particles as cores so as to produce droplets of the working liquid; and a counter part for counting the droplets of the working liquid, wherein the saturator part includes a porous member in which the flow path is passed through to form an inlet at a lower side and an outlet at an upper side thereof so that the working liquid is supplied to a predetermined section of the porous member so as to be impregnated into the entire part of the porous member and further includes a housing having an accommodating space for accommodating the porous member, and wherein a gap is formed between an outer peripheral surface of the porous member and an inner peripheral surface of the accommodating space of the housing between the predetermined section to be supplied with the working liquid and the outlet of the flow path.

With this arrangement, the gap prevents the working liquid from wicking between the inner peripheral surface of the housing and the outer peripheral surface of the porous member by an action such as a capillary phenomenon (hereinafter called a capillary phenomenon action). Accordingly, even when the pressure at an inlet of the apparatus changes, the phenomenon that the wicking of the working liquid through a route to be leaked into the flow path to be droplets results in occurrence of a counting error as in the conventional apparatus can be prevented and the measurement accuracy can be improved, as compared with the conventional apparatus.

In this arrangement, it is preferable that the gap is continuously and circumferentially formed.

In this arrangement, if a pressure at a gas introduction port for introducing the measurement targeted gas decreases and a relative pressure at a working liquid introduction port for introducing the working liquid is increased for some reason to be larger than that at the gas introduction port, the working liquid leakage phenomenon mentioned above may become easy to occur. Whereas, by connecting the working liquid introduction port and the measurement targeted gas introduction port and providing a connection pipe for equalizing a pressure at each port, the working liquid leakage phenomenon caused in the conventional apparatus by such a reason can be reduced. Moreover, according to the present invention, even if the pressure at the working liquid introduction port is transiently increased, since the space of the gap functions as a role of a pressure buffer, the working liquid leakage phenomenon can be prevented more reliably in this regard.

If a non-porous member is arranged inside the porous member, since the volume of the porous member is reduced by the non-porous member, the porous member is prevented from absorbing the working liquid unnecessarily too much, and hence the leakage of the working liquid caused by expansion of air bubbles in the porous member can be also reduced.

Advantageous Effects of Invention

In this way, according to the present invention, by providing the gap, it is possible to prevent the wicking of the working liquid by a capillary phenomenon action between the inner peripheral surface of the housing and the outer peripheral surface of the porous member, and hence it becomes possible to prevent the phenomenon such that the working liquid as remaining in a liquid state rises and leaked into the flow path to cause a counting error, whereby the measurement accuracy can be improved.

DESCRIPTION OF EMBODIMENTS

The following describes a particle number counting apparatus 100 pertaining to the present embodiment with reference to the accompanying drawings.

Figure 1:
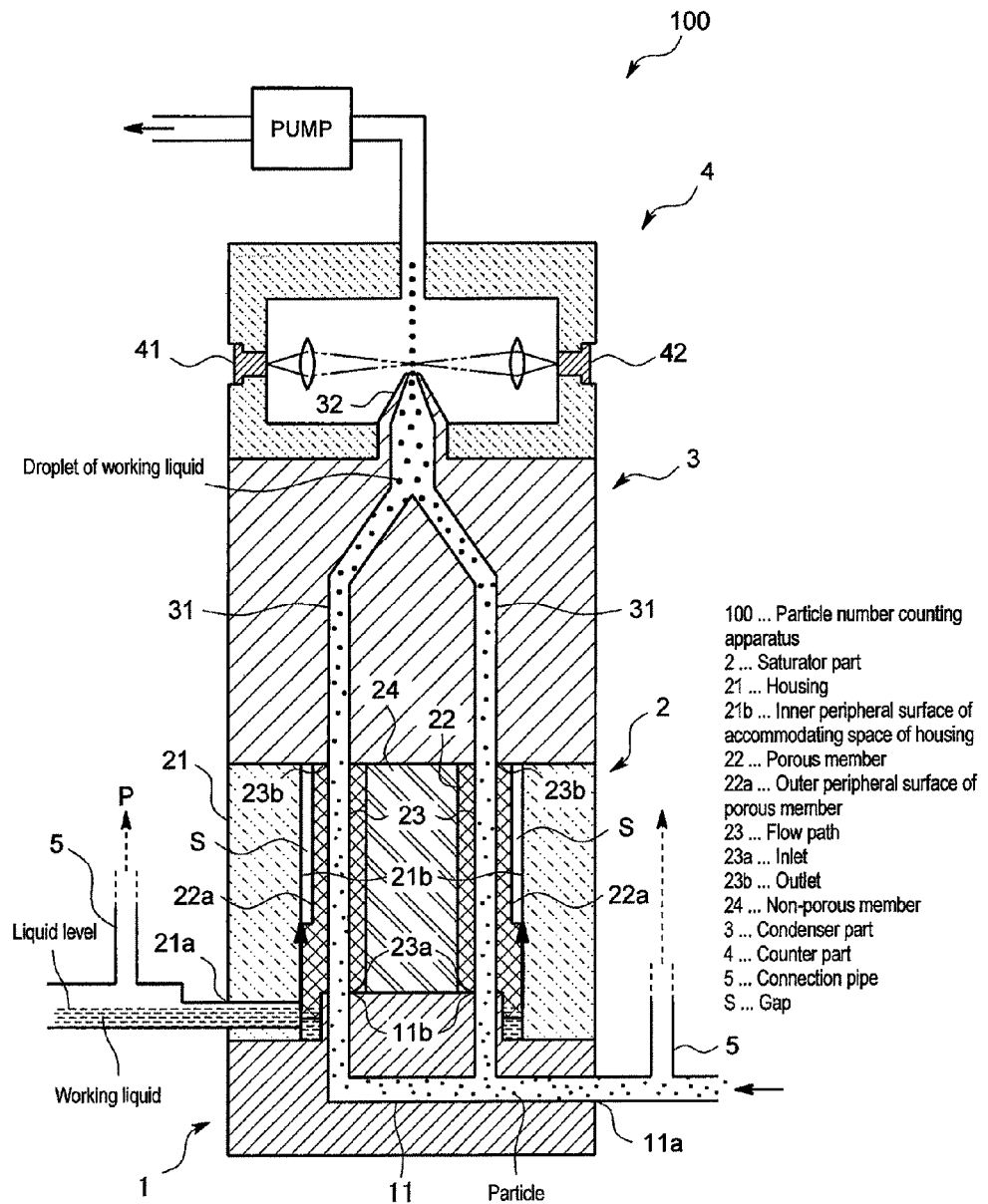
FIG. 1 is a schematic sectional view showing an internal structure of a particle counting apparatus in one embodiment of the present invention.

The particle number counting apparatus 100 is adapted to count the number of minute particles in order to measure a concentration of the minute particles contained in a measurement targeted gas (e.g., atmospheric air or an exhaust gas). As shown in FIG. 1, the apparatus 100 includes an introduction part 1 for introducing the measurement targeted gas containing the minute particles, a saturator part 2 for mixing the measurement targeted gas with a saturated vapor of a working liquid (such as alcohol like ethanol and butanol, and water), a condenser part 3 for cooling the mixed gas and condensing the working liquid surrounding the minute particles so as to produce droplets of the working liquid with the minute particles as cores, and a counter part 4 for counting the droplets of the working liquid. Each part of the apparatus 100 is explained below.

The introduction part 1 is formed, e.g., in a block state and includes a gas flow path 11 inside thereof with its one end opened to a side surface of the introduction part 1 to form a gas introduction port 11a and the other ends opened to a top surface thereof to form gas derivation ports 11b.

The saturator part 2 having a column shape is disposed on the introduction part 1 and includes a cylindrical housing 21 vertically extending and a porous member 22 accommodated in an accommodating space inside the housing 21. Flow paths 23 are formed in a manner of vertically penetrating the porous member 22, and inlets 23a opening at the lower edges of the flow paths 23 are connected to the gas derivation ports lib of the gas flow path 11. Further, a working liquid introduction port 21a is formed to be opened to a side in a lower end portion of the housing 21. The working liquid introduction port 21a is connected to a working liquid tank (not shown) so that the working liquid introduced through the working liquid introduction port 21a is supplied to the lower edge portion of the porous member 22 so as to be impregnated into the entire part of the porous member 22 therefrom by a capillary phenomenon.

More specifically, the lower edge portion of the porous member 22 is set to be located lower in height level than the upper edge of the working liquid introduction port 21a, and a liquid level of the working liquid is set to be always present up to a height higher than the lower edge of the porous member 22 so that the lower edge portion of the porous member 22 is held in a state of being immersed in the working liquid all the time.

In addition, the housing 21 is provided with a temperature controller (not shown) and the inside of the housing 21 is kept at a first predetermined temperature so that the vaporized working liquid (also, referred to as "working liquid vapor" hereinafter) is diffused in a state of saturation in the flow paths 23.

The condenser part 3 having a column shape is disposed on the saturator part 2 and also serves as a housing for accommodating the porous member 22. Condensing pipes 31 connected to the outlets 23b at the top of the flow paths 23 are provided inside the condenser part 3. The condensing pipes 31 are set to have a second temperature that is lower than the inside temperature of the saturator part 2. Thus, the working liquid vapor flowing into the condensing pipes 31 from the flow paths 23 is condensed and liquefied with the minute particles similarly flowing into the condensing pipes 31 as the cores so that the minute particles are enlarged to form droplets of the working liquid each having diameter larger than that of each particle as already described. The droplets of the working liquid are sequentially ejected through a nozzle 32 formed at a top of the condensing pipes 31 in a manner of being not overlapped.

The counter part 4 includes a light emitting part 41 such as, e.g., a laser or a LED for emitting light and a light receiving part 42 such as a photo-sensor for receiving the light, and these parts 41 and 42 are arranged such that the droplets of the working liquid ejected from the nozzle 32 are passed on an optical axis therebetween. In this arrangement, the light is diffused every time the droplets of the working liquid pass on the optical axis to thereby cause a change in light intensity in the light receiving part 42. Thus, the changes in light intensity are counted by a data processing part (not shown) so as to count the droplets of the working liquid.

Figure 2:
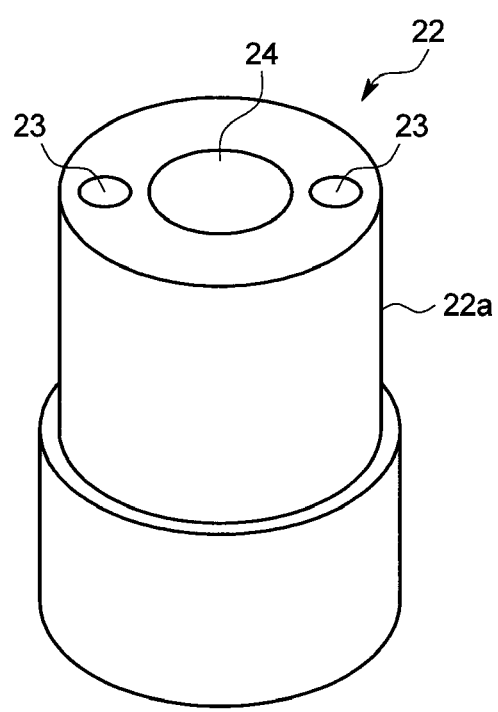
FIG. 2 is a perspective view of a porous member in the same embodiment.

Thus, in the present embodiment, a circumferential gap S is provided on a predetermined region of the porous member 22 to which the working liquid is supplied, i.e., between an outer peripheral surface 22a of the porous member 22 and an inner peripheral surface 21b of the accommodating space of the housing 21 in a region at least an upper side than the liquid level of the working liquid in the porous member 22. To be more specific, in the present embodiment as shown in FIGS. 1 and 2, an upper half of the porous member 22 is reduced in diameter to have a smaller diameter and a lower half thereof is increased in diameter to have a larger diameter, and the lower half is fitted into the accommodating space of the housing 21 so that the gap S having a width not to cause a capillary phenomenon is formed between the outer peripheral surface 22a of the upper half and the inner peripheral surface 21b of the accommodating space of the housing.

In addition, in the present embodiment, a plurality of through holes are provided in a central axis portion of the porous member 22 and a non-porous column member 24 having a predetermined property of non-absorbing the working liquid inside thereof is inserted into the through holes without looseness. The non-porous member 24 is made of, e.g., a resin material having a predetermined rigidity and is fixed to a top surface of the introduction part 1 with screw or the like (not shown). Moreover, in this case, the gas introduction port 11a and the working liquid introduction port 21a are connected by a connection pipe 5 therebetween so that the pressures thereof are equalized.

According to this configuration, as shown by arrows in FIG. 1, the gap S prevents the working liquid from wicking by a capillary phenomenon action between the inner peripheral surface 21b of the housing 21 and the outer peripheral surface 22a of the porous member 22.

Therefore, the phenomenon that the wicking of the working liquid through a route to be leaked into the flow path to be droplets results in occurrence of a counting error as in the conventional apparatus can be prevented and the measurement accuracy can be improved.

Moreover, if a pressure at the working liquid introduction port 21a is increased for some reason to be larger than that at the gas introduction port 11a, the working liquid leakage phenomenon mentioned above may become easy to occur. Whereas, in the present embodiment, by connecting the working liquid introduction port 21a and the gas introduction port 11a so as not to cause a substantial pressure difference. In addition, according to the present invention, even if the pressure at the working liquid introduction port 21a is transiently increased, since the space of the gap S functions as a role of a pressure buffer, the working liquid leakage phenomenon can be prevented more reliably.

Further, since the volume of the porous member 22 is reduced by the non-porous member 24, the porous member 22 is prevented from absorbing the working liquid unnecessarily too much, and hence the leakage of the working liquid caused by expansion of air bubbles in the porous member 22 can be also reduced. In addition, the non-porous member 24 reliably performs a positioning of the porous member 22 and also plays a role of appropriately keeping the gap between the outer peripheral surface 22a of the porous member 22 and the inner peripheral surface 21b of the housing 21. It is noted that the present invention is not limited to the embodiment described above.

Figure 3:
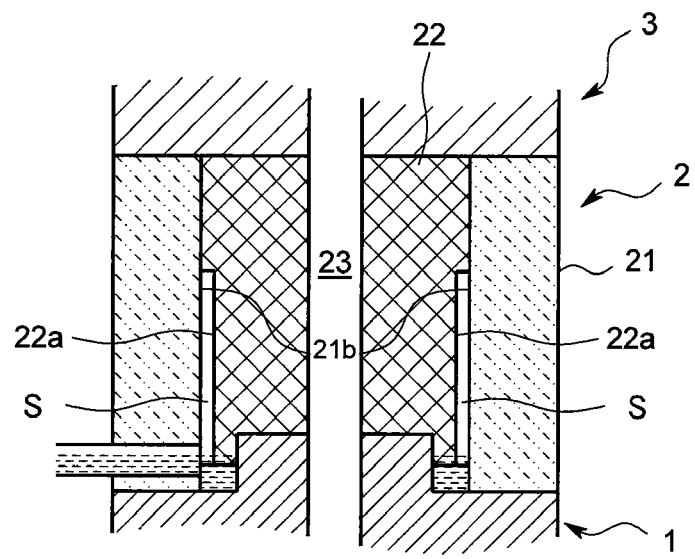
FIG. 3 is a schematic sectional view showing a saturator part in another embodiment of the present invention.
Figure 4:
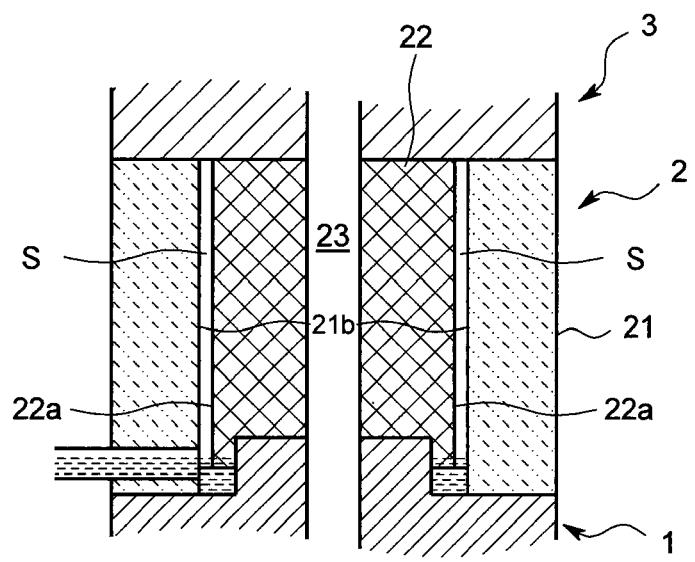
FIG. 4 is a schematic sectional view showing a saturator part in further another embodiment of the present invention.
Figure 5:
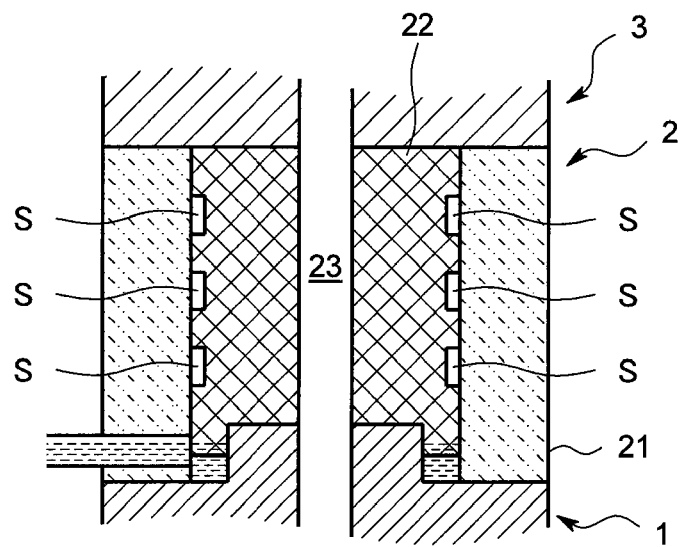
FIG. 5 is a schematic sectional view showing a saturator part in further another embodiment of the present invention.
Figure 6:
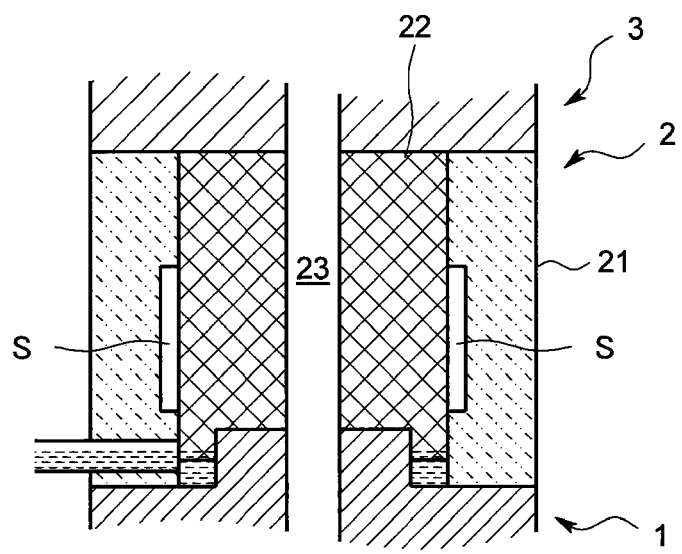
FIG. 6 is a schematic sectional view showing a saturator part in further another embodiment of the present invention.
Figure 7:
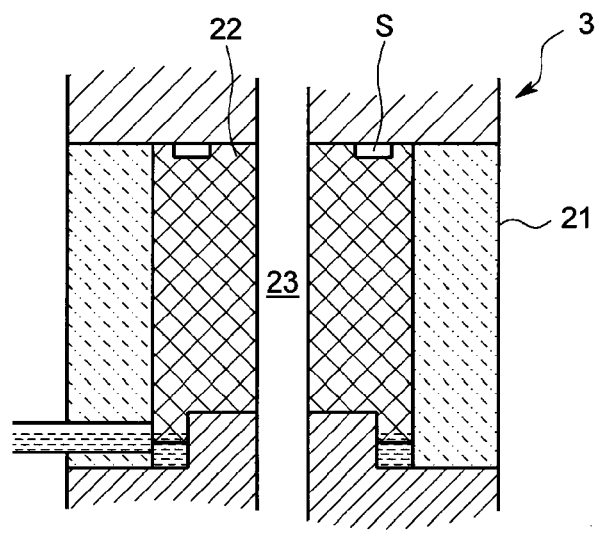
FIG. 7 is a schematic sectional view showing a saturator part in further another embodiment of the present invention.

For example, the gap S may be formed on the lower half of the porous member 22 as shown in FIG. 3, and it may be also formed from a top to a bottom of the porous member 22 as shown in FIG. 4. Also, multi-circumferential such gaps S may be formed as shown in FIG. 5. Instead of providing on the side of the porous member, there may be provided a circumferential recess around the inner peripheral surface 21b of the housing 21 to be formed as a gap S as shown in FIG. 6. Furthermore, as shown in FIG. 7, a circumferential gap S may be formed in an outer peripheral side than the flow path 23 on the top surface of the porous member 22. In this way, it is preferable that the gap S is circumferentially continuous, that is, a close-contacting face between the inner peripheral surface of the housing 21 and the outer peripheral surface of the porous member 22 are interrupted in a region from the working liquid immersion surface of the porous member 22 to the outlet 23b of the flow path 23.

Figure 8:
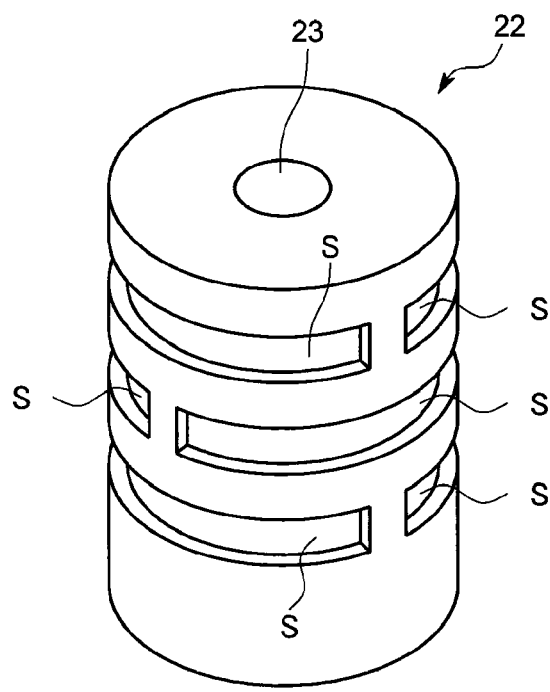
FIG. 8 is a schematic sectional view showing a porous member in further another embodiment of the present invention.
Figure 9:
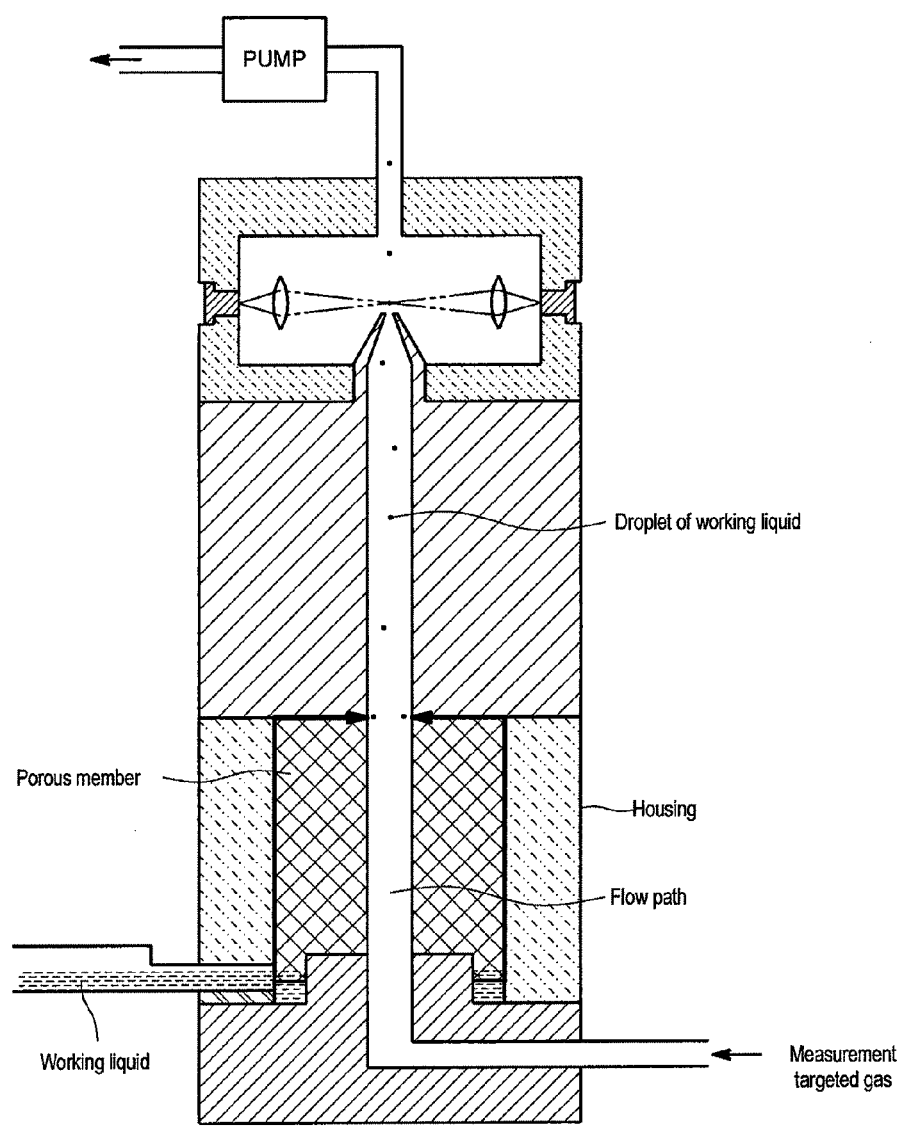
FIG. 9 is a schematic sectional view showing an internal structure of a conventional particle counting apparatus.

However, even if the gap S is partly cut off, a certain effect can be obtained. For example, as shown in FIG. 8, the gap S may be multiplexed such that the cut-off parts are displaced in position. In short, it is sufficient to provide the gaps S in necessary positions so that the distance of the working liquid wicking along a route from the working liquid immersion portion of the close-contacting face to the outlet 23b of the flow path 23 is increased or the area of the close-contacting face is reduced. Moreover, as shown in FIGS. 3 to 8, the non-porous member and the connection pipe are not necessarily required, and even without these members, the measurement accuracy can be remarkably improved than in the conventional apparatus.

In a case when a cylindrical porous member 22 is used (FIG. 4), it is preferable that a gap S with a width about 0.5 mm-2.0 mm, more preferably about 1.0 mm, should be provided. Also, when a porous member is formed with an upper half and a lower half while a diameter of the lower half is larger than a diameter of the upper half (refer to FIG. 2), the gap S to prevent a capillary phenomenon may be made larger for example up to about 6.0 mm. When the thickness in a radial direction of the porous member 22 is too small, the strength at a fitting portion (lower end part) for fitting into and holding within an accommodating space of a housing 21 cannot be obtained, thereby possibly causing the leakage of the working liquid. As the diameter of the upper half is made smaller by for example making the diameter of the lower half larger, the strength at the fitting portion (lower end part) can be obtained compared to when simply making it in a cylindrical shape while the capillary phenomenon can be reliably prevented as the gap S is made larger. Here, the width of the gap S such as 2.0 mm and 6.0 mm is a value considered the strength at the portion for fitting into and holding, the thickness in a radial direction of the porous member 22, the amount capable of impregnation of the working liquid, etc., and the gap S may be made larger according to the scope of the invention as long as the strength, the thickness or the amount is obtained by varying the shape or the structure of the porous member 22.

In addition, the present invention is not limited to the above embodiments, and it is needless to say that the embodiments and modified embodiments may be partly combined appropriately, and various changes and modifications can be made within the scope of the present invention unless departing from the spirit thereof.

REFERENCE SIGNS LIST

100 . . . Particle number counting apparatus
2 . . . Saturator part
21 . . . Housing
21b . . . Inner peripheral surface of accommodating space of housing
22 . . . Porous member
22a . . . Outer peripheral surface of porous member
23 . . . Flow path
23a . . . Inlet
23b . . . Outlet
24 . . . Non-porous member
3 . . . Condenser part
4 . . . Counterpart
5 . . . Connection pipe
S . . . Gap

The invention claimed is:

1. A particle number counting apparatus comprising:
a saturator part including a flow path in which a working liquid is diffused in a vaporized state so as to render sample particles contained in a measurement targeted gas to flow in the flow path;
a condenser part for introducing the sample particles and vaporized working liquid from the flow path and condensing the working liquid with the sample particles as cores so as to produce droplets of the working liquid; and
a counter part for counting the droplets of the working liquid,
wherein the saturator part includes a porous member in which the flow path is passed through to form an inlet at a lower side and an outlet at an upper side thereof so that the working liquid is supplied to a predetermined section of the porous member so as to be impregnated into the entire part of the porous member, and a housing having an accommodating space for accommodating the porous member, wherein a gap is formed between an outer peripheral surface of the porous member and an inner peripheral surface of the accommodating space of the housing, the gap providing an open space free of any material at least in an upper side opposite the predetermined section of the porous member to be supplied with the working liquid.

2. The particle number counting apparatus according to claim 1, wherein the gap is continuously and circumferentially formed.

3. The particle number counting apparatus according to claim 1 further comprising a connection pipe connecting a working liquid introduction port for introducing the working liquid and a measurement targeted gas introduction port for introducing the measurement targeted gas so as to equalize a pressure at each of the ports.

4. The particle number counting apparatus according to claim 1, wherein the porous member has a non-porous member arranged inside thereof.

5. A saturator part adapted to a particle number counting apparatus which comprises:

the saturator part including a flow path in which a working liquid is diffused in a vaporized state so as to render sample particles contained in a measurement targeted gas to flow in the flow path;

a condenser part for introducing the sample particles and vaporized working liquid from the flow path and condensing the working liquid with the sample particles as cores so as to produce droplets of the working liquid; and a counter part for counting the droplets of the working liquid, the saturator part including:

a porous member in which the flow path is passed through to form an inlet at a lower side and an outlet at an upper side thereof so that the working liquid is supplied to a predetermined section of the porous member so as to be impregnated into the entire part of the porous member; and a housing having an accommodating space for accommodating the porous member;

wherein a gap is formed between an outer peripheral surface of the porous member and an inner peripheral surface of the housing at least in an upper side opposite the predetermined section of the porous member to be supplied with the working liquid, the gap being an open space free of any material.

6. The particle number counting apparatus according to claim 2 further comprising a connection pipe connecting a working liquid introduction port for introducing the working liquid and a measurement targeted gas introduction port for introducing the measurement targeted gas so as to equalize a pressure at each of the ports.

7. The particle number counting apparatus according to claim 2, wherein the porous member has a non-porous member arranged inside thereof.

8. The particle number counting apparatus according to claim 3, wherein the porous member has a non-porous member arranged inside thereof.

9. The saturator part of claim 5 wherein the gap formed between the outer peripheral surface of the porous member and the inner peripheral surface of the housing is sized to prevent a capillary phenomenon action when liquid is present.

10. The saturator part of claim 9 wherein the gap is continuously and circumferentially formed.

11. The particle number counting apparatus of claim 1 wherein the gap formed between the outer peripheral surface of the porous member and the inner peripheral surface of the housing is sized to prevent a capillary phenomenon action when liquid is present.

12. The particle number counting apparatus of claim 11 wherein the gap is continuously and circumferentially formed.

13. A particle number counting apparatus comprising:

a saturator part comprising a housing with an interior accommodating space and a porous member contained within the interior accommodating space, the porous member having a lower side, an upper side and a flow path passing therethrough extending from the lower side to the upper side, the flow path having an inlet on the lower side of the porous member and an outlet on an upper side of the porous member, wherein a working liquid is supplied to a predetermined section of the porous member so as to be impregnated into the entire part of the porous member, and wherein the working liquid is diffused in a vaporized state so as to cause sample particles contained in a measurement targeted gas to flow in the flow path, wherein a gap is formed between an outer peripheral surface of the porous member and an inner peripheral surface of the accommodating space of the housing at least in an upper side away from the predetermined section of the porous member which is supplied with the working liquid, the gap being free of material and sized to prevent wicking of the working liquid along the gap;

a condenser part for introducing the sample particles and vaporized working liquid from the flow path and condensing the working liquid with the sample particles as cores so as to produce droplets of the working liquid; and a counter part for receiving and counting the droplets of the working liquid.

14. The particle number counting apparatus according to claim 11, wherein the gap is continuously and circumferentially formed.

15. The particle number counting apparatus according to claim 11 further comprising a connection pipe connecting a working liquid introduction port for introducing the working liquid and a measurement targeted gas introduction port for introducing the measurement targeted gas so as to equalize a pressure at each of the ports.

16. The particle number counting apparatus according to any one of claim 11, wherein the porous member has a non-porous member arranged inside thereof.

* * * * *